United States Patent [19]

Puritch et al.

[11] Patent Number: 5,510,110
[45] Date of Patent: Apr. 23, 1996

[54] CHEMICAL MOLLUSC BARRIER

[75] Inventors: George S. Puritch, Saanichton; David S. Almond; Robert M. Matson, both of Victoria, all of Canada

[73] Assignee: W. Neudorff GmbH KG, Emmerthal, Germany

[21] Appl. No.: 107,239

[22] Filed: Aug. 16, 1993

Related U.S. Application Data

[63] Continuation-in-part of Ser. No. 72,538, Jun. 4, 1993, abandoned.

[51] Int. Cl.$^6$ ..................................... A01N 25/34
[52] U.S. Cl. ..................... 424/421; 424/408; 424/409; 424/414; 424/416; 424/417; 424/405; 424/403
[58] Field of Search .................. 424/405, 409–415, 424/419, 420, 421, 408, 416, 417; 574/920, 557, 558; 43/124, 131; 504/320; 106/2, 17, 18, 243; 252/34, 39, 89.1, 96, 98, 107, 108, 117, 120, 367–369

[56] References Cited

U.S. PATENT DOCUMENTS

| | | | |
|---|---|---|---|
| 3,234,138 | 2/1966 | Carroll et al. | 252/117 |
| 4,471,562 | 9/1984 | Brucker | 43/108 |
| 4,659,736 | 4/1987 | Schluter et al. | 514/452 |
| 4,707,496 | 11/1987 | Simmons | 514/531 |
| 4,747,230 | 5/1988 | Zalesky | 43/121 |
| 4,756,116 | 7/1988 | Cutter | 43/108 |
| 4,821,452 | 4/1989 | Beckley | 43/131 |
| 4,826,685 | 5/1989 | Stewart | 424/410 |
| 4,906,653 | 3/1990 | Kiehs et al. | 514/388 |
| 4,992,471 | 2/1991 | Longhurst | 514/613 |
| 5,162,349 | 11/1992 | Beriger | 514/363 |
| 5,296,226 | 3/1994 | Askham | 424/405 |
| 5,401,500 | 3/1995 | Warren et al. | 424/84 |

FOREIGN PATENT DOCUMENTS

WO90/08471  2/1990  WIPO.

OTHER PUBLICATIONS

Textbook of Biochemistry—West et al. 4th Edition 1966, pp. 139, 140:Fats.
Hackh's Chemical Dictionary 4th Edition Grant, Ed. 1969, p. 486:Palm.

*Primary Examiner*—Thurman K. Page
*Attorney, Agent, or Firm*—William C. Geary, III; Lahive & Cockfield

[57] ABSTRACT

A chemical barrier effective to irritate and repel molluscs contains an active ingredient formed of fatty acid salts of monocarboxylic acids having chain lengths ranging from 8 to 14 carbon atoms, coconut fatty acid, palm kernel fatty acid, and mixtures thereof. The barrier may be in the form of a solid or a gel-like material that is able to harden to a solid. A solid barrier may also be formed by providing a solid substrate coated with the active ingredient barrier composition.

22 Claims, No Drawings

CHEMICAL MOLLUSC BARRIER

REFERENCE TO RELATED APPLICATION

This is a continuation-in-part of U.S. patent application Ser. No. 072,538 filed Jun. 4, 1993 now abandoned.

BACKGROUND OF THE INVENTION

This invention relates to methods and compositions for protecting agricultural and horticultural land from damage and infestation by molluscs.

Terrestrial pulmonate gastropods, slugs and snails (collectively molluscs) are significant plant pests that affect commercial agriculture, horticulture and domestic gardens. These molluscs are omnivores and consume large amounts of vegetative material during their daily foraging. Consequently, they can seriously damage vegetable gardens and even plant crops during all phases of the plant growing cycle. The degree of damage they cause is dependent upon the activity and density of the molluscs and on their feeding habits. Each species of mollusc has feeding preferences that differ. For example, Arion Rufus (L.) prefers the Solanaceae and Compositae, while *Deroceras reticulatum* (Müller) selects Leguminosae, Cruciferae, Compositae, carrot roots, potato leaves and tubers, cereals and seedlings. *Arion hortensis* Fér seeks out living plants, carrot roots, tubers and bulbs. Control measures are necessary to ensure adequate protection of growing plants from the destructive potential of molluscs.

A wide variety of approaches have been attempted to control and combat pests or molluscs. Perhaps the most common is the use of poisonous compounds called molluscicides. Molluscicides can comprise a variety of chemical compounds including table salt (NaCl), calcium arsenate, copper sulfate and metaldehyde. Metaldehyde, synthesized by the polymerization of acetaldehyde in suspension in ethanol in the presence of an acidic catalyst, has become the most common molluscicide in commercial use.

A major drawback of most molluscicides is that they are contact killers and that they have little effect if molluscs do not come into direct physical contact with the molluscicide, Thus, if a sprayed molluscicide does not contact molluscs, or if molluscs migrate into an area after spraying, the molluscicide typically does not affect the molluscs, This lack of residual action is a major problem for many molluscicides, Metaldehyde, however, has the advantage of providing contact toxicity as well as acting as an ingested toxin. As a result, this compound is useful as a long lasting bait, serving to attract the molluscs and to kill them after ingestion of the compound. Despite its high degree of effectiveness and its commercial popularity, metaldehyde is toxic to higher mammals and is a major, worldwide contributor to domestic animal poisoning.

Mollusc control is also effected by mechanical trap devices. These devices are of a variety of designs, including those described in U.S. Pat. Nos. 4,821,452 and 4,747,230. These devices are generally designed to attract molluscs and then entrap them. Mortality results either by molluscicide baits or by watertraps that drown the molluscs. Although traps can be effective, they require continual tending to remove dead molluscs and to add fresh bait. Another drawback of such devices is that they are effective only over a relatively small area.

Chemical and/or mechanical barriers also are effective mollusc control devices that bar mollusc entry into a protected area. A typical mechanical barrier, described in U.S. Pat. No. 4,756,116, consists of a pair of dissimilar metal strips that cause an electrolytic charge when the molluscs attempt to cross the strips. Another example of a mechanical barrier is copper strips that are placed around trees or flower beds. Chemical barriers are usually compounds that are highly irritating to molluscs and deter them from crossing the barrier. Known chemical barriers include lime, fine sawdust, diatomaceous earth, ash, egg shells, metaldehyde, and table salt. One problem inherent with known chemical barriers is their lack of residual action. To be effective these barriers must have sufficient solubility to dissolve in the molluscs' proteinacious slime. However, this solubility can also cause the barrier to disintegrate quite rapidly in the warm, moist environments that molluscs commonly inhabit. The result is that the chemical barriers quickly lose their potency. To offset the tendency of chemical barriers to disintegrate in the environment, chemical barriers have sometimes been embedded in a long lasting matrix such as a polymer. One commercial product known as "Slug and Snail Defense" sold by C. D. McGarr Enterprises, consists of a sodium chloride-impregnated plastic barrier.

Accordingly, improved chemical barriers are needed to control and prevent damage by molluscs to crops, plants and trees.

Accordingly, an object of the invention is to provide a chemical mollusc barrier that is both effective and environmentally compatible. Another object of the invention is to provide such a barrier having sufficient solubility to irritate and repel molluscs, and having sufficient ability to resist environmental degradation to be effective for a suitable length of time. A further object is to provide such a barrier that can be economically used to effectively protect sizable agricultural or horticultural plots. Other objects of the invention will be apparent from the disclosure that follows.

SUMMARY OF THE INVENTION

The present invention comprises methods and compositions for repelling terrestrial molluscs and thus protecting agricultural and horticultural land from infestation by molluscs. In one aspect the invention relates to a chemical barrier composition for repelling molluscs. The barrier preferably comprises an active ingredient that is effective against molluscs as an irritant and a repellent. The active ingredient preferably is formed of the sodium, potassium, and/or ethanolamine salts of monocarboxylic fatty acids having from 8 to 14 carbon atoms, coconut fatty acid, palm kernel fatty acid, or mixtures of such fatty acids. Preferably, the active ingredient comprises, at least, about 10% by weight of the barrier composition. The barrier can also include a solvent that can be selected from among water, alcohols, diols, triols, and mixtures thereof. The barrier of the present invention is sufficiently soluble to dissolve in molluscs' proteinacious slime. At the same time, however, the barrier composition is not so soluble that it will prematurely dissolve or degrade in the environment. The barrier thus is able to remain effective in the environment for a suitable length of time even when subject to rainfall. The barrier can remain effective for at least about seven days, and in some circumstances for up to two weeks.

The barrier composition can be in the form of a solid material, such as in pelletized, granular or powdered form. Alternatively, the barrier composition can be in the form of a viscous, flowable material that can rapidly harden to a solid mass upon exposure to the environment. The barrier composition can also be in the form of an inert substrate coated with the mollusc-repelling active ingredient of the invention. Colorants may be added to either the solid or the flowable barrier composition so that it will achieve the same color as the background against which it is used.

In another aspect, the invention is directed to a method of preventing terrestrial molluscs from infesting and attacking plants. The method involves providing a chemical barrier composition of the type described above and applying the barrier in a continuous strip to prevent intrusion and infestation by terrestrial molluscs beyond the barrier. The barrier may be applied about the perimeter of an area containing living plants, or it may be applied as a band about a tree trunk to prevent molluscs from infesting the foliage of the tree.

DETAILED DESCRIPTION OF THE INVENTION

The invention comprises an environmentally compatible, fatty acid salt-based chemical barrier that irritates and repels slugs. The barrier comprises one or a mixture of salts of fatty acids having a chain length ranging from 8 to 14 carbon atoms. The barrier can be prepared in the form of solid granules, flakes or a powder derived from a solid, fatty acid salt composition that is either substantially pure or composed predominantly of the fatty acid salt. Alternatively, the barrier can be in the form of a viscous, fluid material that can rapidly harden to a solid material upon exposure to the environment. Such a viscous fluid composition comprises one or more fatty acid salts combined with a solvent and one or more formulation enhancing additives such as carnauba wax, lanolin wax, ceresine wax, Japan wax, beeswax, and kester wax. The wax additives are effective to thicken and stabilize the barrier formulation. They are also believed to be effective to improve the weathering ability of the barrier.

An important advantage of the chemical barrier of the present invention is the weather resistance properties that it possesses. The barrier is able to resist degradation caused by moisture and rainfall and can remain effective for at least about seven days, and in some circumstances for two weeks or longer.

In most circumstances the barrier is applied about a perimeter of an area within which it is desired to prevent intrusion and infestation by molluscs. The barrier is effective to irritate and repel slugs both when it is wet and when it is dry.

As noted above, the barrier preferably is comprised of fatty acid salts having about 8 to 14 carbon atoms, coconut fatty acid salt, palm kernel salt, or mixtures of such fatty acid salts. Preferably, the fatty acid salts that comprise the barrier are those that are sufficiently soluble to dissolve in the proteinacious slime of molluscs, but that are not so soluble that they rapidly dissolve and become ineffective upon exposure to moisture or rainfall. Another requirement of the fatty acid salts used to form the barrier of the invention is that they be irritating to slugs.

Long chain fatty acids (i.e., C-16 and higher) have been found to be ineffective to irritate and repel slugs. Medium chain fatty acids (i.e., C-8 to C-14), have surprisingly been found to be highly irritating to molluscs and are able to repel and irritate the molluscs. However, the various fatty acid salts within the range of medium chain fatty acids have different levels of irritability and of ability to withstand dissolution in water. Generally, lower chain length fatty acid salts have a greater degree of mollusc irritability, but are more soluble in water. Fatty acid salts with higher chain lengths tend to have a lower level of irritability, but a greater ability to withstand dissolution in water. For example, the C-8 fatty acid salts have been found to have the highest level of irritability among fatty acid salts in the C-8 to C-14 fatty acid salts, but these salts are also the most soluble and least residual. Conversely, the C-14 fatty acid salts are the least soluble in water, but tend to be less irritating to molluscs than are the C-8 salts.

Preferred fatty acid salts, useful as barrier composition active ingredients include salts of caprylic acid, pelargonic acids, capric, acid, undecanoic acid, lauric acid, and myristic acid. Among the most preferred fatty acid salts, useful alone as active ingredients in the barrier, are salts of capric, undecanoic, and lauric acids. The preferred salts of such acids include the sodium, potassium, and ethanolamine salts. Sodium salts tend to be the most preferred salt, however, it is possible to use blends of sodium and potassium salts.

Fatty acid salts having chain lengths in the C-8 to C-14 range have different solubilities and different abilities to irritate molluscs; therefore it is often advantageous to form an active ingredient using mixtures of fatty acid salts. Typically, one would combine one or more fatty acid salts having a high degree of mollusc irritability with one or more fatty acid salts having a lower level of mollusc irritability, but a somewhat lesser solubility in water. Preferred blends include the sodium salt of lauric acid combined with the sodium salt of capric acid. The ratio of the C-12 fatty acid salts to the C-10 fatty acid salts can range from 2:8 to 8:2, by parts and preferably the ratio is approximately 7:3 by parts. Another useful fatty acid salt blend is the combination of the sodium and/or potassium salts of myristic acid and capric acid at ratios, by parts, ranging from 2:8 to 9:1, and most preferably at a ratio of about 8:2. Blends of the sodium and/or potassium salts of C-14, C-12, and C-10 fatty acids are also useful. Such blends can be used at a range of ratios, and most preferably at ratios of about 6:2:2 and 5:2:3.

In addition to the individual fatty acid salts mentioned above, the active ingredient of the barrier may also be formed of salts of fatty acids that themselves are blends of fatty acids, such as coconut fatty acid, palm kernel fatty acid or others. Such salts of fatty acid blends may also be combined with individual fatty acid salts having chain lengths in the range of C-8 to C-14. A representative example of such a blend is 7 parts sodium coconate to 3 parts sodium caprylate.

One of ordinary skill in the art will appreciate that the preferred fatty acid salt or fatty acid salt mixture can be determined by balancing the irritability and solubility of the salt. Once it is established that a particular fatty acid salt (or mixture) is sufficiently irritating to molluscs, the fatty acid salt or mixture is then evaluated for its ability to withstand weather. Acceptable compositions are those that are able to withstand weathering for approximately 14 days.

Solid mollusc barriers can be formed of substantially pure forms of fatty acid salts of the types noted above. Alternatively, the fatty acid salt active ingredient may be present in the barrier at a concentration ranging from about 5 to 95% by weight, and more preferably at about 10 to 50% by weight. The solid barrier may also include a colorant that enables the barrier to match its environmental background. Further, the barrier may also include binder or carrier material such as talc, clay, alginates, waxes, silicates, and latexes.

Gel- or paste-like compositions that rapidly harden upon exposure to air may also be used to form the barrier of the invention. The gel or paste-like compositions can be prepared by combining the desired fatty acid salt or fatty acid salt mixture, of the type described above, with one or more solvents. Suitable solvents include water, alcohols, diols, triols and mixtures thereof. Specific examples of suitable solvents include ethanol, isopropyl alcohol, propylene glycol, methanol, glycerol, and tetrahydrofurfural alcohol. Other formulation enhancing additives can include clays, alginates, waxes, or acrylic polymers. Gel-like compositions may also include a suitable colorant to enable the barrier to match the background against which it is used. Such gel-like formulations are easy to apply and rapidly harden (i.e., within about 1 hour) to the consistency of a wax or a putty. These formulations then solidify to the consistency of a hard soap within about 24 hours.

In one embodiment about 20 to 50% by wt. of a dry, powdered fatty acid salt active ingredient is added to a 40% latex emulsion in water to yield a barrier with improved weathering properties. Similarly, about 10 to 20% by wt. of a 40% latex emulsion can be incorporated into a gel-like barrier composition.

Both the solid and gel-like formulations have the advantage of resisting degradation in normal environmental conditions, including rainfall, for a suitable length of time, and normally for about 7 to 14 days.

Gel-like formulations may include a fatty acid salt active ingredient in a concentration ranging from about 5 to 60% by weight, and more preferably at a concentration range of about 10 to 50% by weight.

Suitable colorants useful with both solid and gel-like barriers are commercially available from Sun Chemical Company as black iron oxide and brown iron oxide.

As noted above, the barrier compositions of the invention can be applied as solid granules or powders, or as a viscous paste that is able to harden. Solid materials in the form of powders, granules, flakes, and the like can be applied as a substantially continuous strip or border around an area containing plants, within which it is desired to prevent intrusion and infestation by molluscs. Although the amount of barrier material applied can vary, the barrier typically is applied in a strip that is approximately 2.5 centimeters wide and 0.5 cm deep. If desired, two substantially parallel strips can be applied. Viscous gel-like barriers can be similarly applied around an area within which it is desired to prohibit infestation by molluscs. In addition, such compositions may be applied in a strip about the trunk of the tree to prevent molluscs from infesting and damaging the foliage of trees.

Alternatively, solid mollusc barriers can be formed of substantially solid substrate materials that are coated with the active barrier composition of the invention. The substrate materials preferably are entirely coated with the active barrier composition. A variety of inert solid material may serve as the substrate materials for the invention. Examples of suitable inert substrates include stones, pebbles, lava rocks, wood chips, bark, bean seeds, dried peas, granulated plastic materials, plastic strips, paper, paperboard, and similar materials.

The term "inert" is used to indicate that the substantial solid substrates do not react with the active barrier composition and are not, by themselves, effective to repel molluscs.

The substrates preferably are entirely coated with a gel-or paste-like composition of the type described above. The coating process can be effected by contacting the substrate (e.g., by dipping or spraying) with the active barrier composition and then allowing the active barrier coating to dry on the substrate. It is also possible to coat the substrates by combining the substrate with a suitable amount of dry active ingredient, pressurizing and heating (e.g., to about 100° C.) these components to melt the active ingredient, agitating the components so as to entirely coat the substrate, and allowing the coated substrate to dry.

The substrate materials can have varying sizes and shapes. An example of a suitable substrate material is one having a diameter in the range of about 3 mm to about 5 cm. The coating should be applied to the substrate in a continuous manner and the coating thickness should be in the range of about 0.5 mm to 3 cm.

The barrier composition of the present invention is effective against a variety of molluscs, including: *Ariolimax spp.; Arion species* including *Arion ater, A. hortensis, A. rufus, A. circumscriptus, A. empericorum; Deroceras spp.; Agriolimax spp.; Prophysaon spp.; Helix pomata*; and *Cepaea nemoralis*.

An exemplary barrier composition having as an active ingredient a blend of sodium laurate and sodium caprate at a ratio of 7:3 can be prepared as follows. Distilled water (25.63 wt. %) is added to 20.0 wt. % of propylene glycol. Sodium hydroxide (18.49 wt. % of a 40.5 wt. % solution) is then added and the mixture is heated to about 70° C. Thereafter, lauric acid (25.24 wt. %) and capric acid (10.64 wt. %) are added to the basic solution and stirred to cause total saponification yielding a fatty acid salt concentration of about 40 wt. %. The liquid soap is then cooled to form a viscous, cream-like mass and placed in molds to dry. Upon drying the composition can be pelletized or powdered for ease of application. Alternatively, a gel-like barrier can be obtained by omitting the drying step and maintaining the composition in a gel-like state.

A barrier composition, prepared as described above, can be coated upon a substrate by a variety of techniques. In one embodiment the barrier composition can be in liquid form and be sprayed upon the substrate. For example, dried pea substrates can be coated by spraying about 1 Kg of dried peas with about 840 g of a barrier solution maintained at about 60° C. During spraying the peas should be tumbled or agitated to ensure a substantially uniform coating. Such a technique will achieve a substantially uniform barrier coating (of about 2 mm thick) on the peas that will dry and harden almost immediately.

Alternatively, a substrate, such as dried peas, can have a barrier coating applied using a solid barrier starting material. This can be accomplished by placing the substrate and the solid barrier composition together in a coating vessel and agitating the contents while heating to about 100° C. and maintaining the pressure slightly in excess of ambient. A suitable pressure is approximately 100 psi, however, the optimal pressure may be varied as will be understood by one of ordinary skill in the art.

The following examples serve to further illustrate the invention.

EXAMPLE 1

The sodium salts of various fatty acids, using an alcohol solvent, were prepared at a concentration of 20 wt. % active ingredient according to the general process noted above. The salts were also diluted to concentrations of 10% and 5%. The salts were poured into small plastic lids and allowed to dry. After the solutions had dried, Ariolimax slugs were selected from outside pens and individually placed on the fatty acid salt composition. Slug responses were noted for slime production and escape from the barrier. After the initial responses were recorded, treatments of 20, 10, and 5% concentrations of sodium laurate were rinsed by placing the lids under a fast running shower for 15 minutes. Slugs were then placed back on the lids and their response was noted. The data obtained are illustrated in Tables 1A and 1B. This data represent visual assessment of the percent of formulation removed.

TABLE 1A

Pre-Wash Evaluation of Fatty Acid Salts

| Active Ingredient (Concentration) | Observations |
|---|---|
| Sodium Octanoate (20%) | Heavy mucous, spiraling and contraction. Salt removed from area contacted. Slug did not cross barrier |
| Sodium Octanoate (10%) | Similar to 20% Results |
| Sodium Octanoate (5%) | Did not solidify - was not tested |
| Sodium Caprate (20%) | Heavy mucous, spiraling and contraction. Salt removed from area contacted. Slug did not cross barrier. |
| Sodium Caprate (10%) | Similar to 20% Results |
| Sodium Caprate (5%) | Did not solidify - was not tested. |
| Sodium laurate (20%) | Moderate slime production, no spiraling or contraction. Salt was not removed from area contacted. |
| Sodium laurate (10%) | Like 20% Results. Slug touched and tested salt but did not cross |
| Sodium laurate (5%) | No spiraling, moderate slime production. Slug would touch salt, but would not cross. |
| Sodium Palmitate (20%) | Little slime production, no spiraling or contraction. Slug crossed salt and did not try to get off |
| Sodium Palmitate (10%) | Like 20% Results |
| Sodium Palmitate (5%) | Very little, if any, reaction. |
| Control (No. A.I.) | No reaction |

TABLE 1B

Post-Wash Evaluation of Sodium Laurate

| Sodium Laurate Concentration | Observations |
|---|---|
| 20% | All treatments similar to pre-wash |
| 10% | Similar to 20% Results |
| 5% | Did not solidify - was not tested. |

EXAMPLE 2

The formulations noted in Table 2A were prepared. For each formulation, 2.5 grams of the solution was poured into a petri dish, spread and allowed to set for 24 hours. After that period, Ariolimax slugs were simultaneously placed on the fatty acid salt barriers and evaluated. Fatty acid salt-coated petri dishes were mounted on an inclined board and placed outdoors, where natural weathering occurred. The data illustrated in Table 2B were collected after two days exposure to weathering and after seven days exposure weathering.

TABLE 2A

Example 2 Formulations

| Formulation No. | Soap Concentration | Ratio | Additives |
|---|---|---|---|
| 1 | 20% sodium laurate | 10:0 | Ethanol |
| 2 | 15% sodium laurate:caprate | 8:2 | Isopropyl alcohol (IPA) |
| 3 | 15% sodium laurate:caprate | 7:3 | IPA |
| 4 | 15% sodium laurate:caprate | 7:3 | Propylene Glycol |
| 5 | 15% sodium myristate | 10:0 | IPA |
| 6 | 15% sodium myristate caprate | 8:2 | IPA |

TABLE 2B

Activity of Sodium Fatty Acid Salts and Loss Due to Weathering

| Formulation No. | Initial Activity (18° C.) | % A.I. Removed @ 2 days | % A.I. Removed @ 7 days | Activity After Weathering (19° C.) |
|---|---|---|---|---|
| 1 | Good | 10 | 50 | Fair |
| 2 | Good | 10 | 50 | Fair |
| 3 | Very Good | 30 | 50 | Fair |
| 4 | Very Good | 100 | 100 | N/A |
| 5 | Poor | 0 | 5 | N/A |
| 6 | Fair | 5 | 5 | Fair |

EXAMPLE 3

The formulations described in Table 3A were prepared. For each formulation, 2.5 grams of solution was poured into a petri dish, spread, and allowed to set for 24 hours. After that period, Ariolimax slugs were simultaneously placed on the fatty acid salt compositions (two slugs per dish) and evaluated. After the assessment, the slugs were removed, and the soap-coated petri dishes were mounted on an inclined board and placed outdoors where natural weathering occurred. The fatty acid salts were assessed and data were collected after one day of exposure and after two days of exposure to weathering. The results illustrated in Table 3B represent a visual assessment of the percent of formulation removed. Heavy rain showers occurred during the exposure period.

TABLE 3A

Example 3 Formulations

| Formulation No. | Soap Conc. | Ratio | Additives |
|---|---|---|---|
| 1 | 15% sodium myristate:sodium:caprate blend | 6:4 | IPA |
| 2 | 15% sodium myristate-sodium:caprate blend | 6:2:2 | IPA |
| 3 | 15% sodium myristate:laurate:caprate blend | 5:2:3 | IPA |
| 4 | 15% sodium laurate:caprate | 8:2 | Monamide |

TABLE 3A-continued

Example 3 Formulations

| Formulation No. | Soap Conc. | Ratio | Additives |
|---|---|---|---|
| | blend | | & IPA |

TABLE 3B

Activity of Sodium Salts and Loss Due to Weather

| Formulation No. | Initial Activity (20° C.) | Initial Activity (11° C.) | % Removed 1 day | % Removed 2 days |
|---|---|---|---|---|
| 1 | Good/V. Good | Good | 40 | 75 |
| 2 | Good | Good | 10 | 50 |
| 3 | Good | Good | 5 | 20 |
| 4 | Good | Good | 30 | 100 |

EXAMPLE 4

A barrier formulation having sodium laurate and sodium caprate (7:3 ratio) was made fresh at an A.I. concentration of 40% by wt. Thin wood veneer was cut into rectangles 1.5 cm×24.0 cm. Four pieces of veneer were treated by spreading formulation to form two substantially parallel bands, each being 2.5 cm wide, lengthwise on the veneer. A gap of 2 cm was left between the two strips. On two pieces of the veneer, the bands were thick (5 mm), while on the other two pieces, the bands were thin (2 mm). The thick strips were left to dry for 48 hrs. and then placed under a shower for 1 hour (about 1 m$^3$ water at 60 psi). The thin strips were dried for 24 hours and then showered. Two strips were put into a laboratory barrier test. The test was set up in planting trays with the slugs and food separated by the treated barriers. Four slugs were placed into each tray. Trays were cleaned after two days, and the number of slugs observed to cross the barriers (as evidenced by slime trails and actual slugs) were recorded (Table 4).

TABLE 4

Example 4 Results

| TREATMENT | 1 DAT* | 2 DAT | 6 DAT | REMARKS |
|---|---|---|---|---|
| Thick strip No. 1 | 0 | 0 | 0 | Slugs skirted edge, no crossing |
| Control No. 1 | 1 | 2 | 2+ | Significant crossing |
| Thick strip No. 2 | 0 | 0 | 0 | No sign of any crossing |
| Control No. 2 | 0 | 2 | 2+ | Slime all over barrier |
| Thin strip No. 1 | 0 | 0 | 2 | Slug went through the bare or very thin section |
| Thin strip No. 2 | 0 | 0 | 0 | Slugs approached edge but never crossed |

*Days After Treatment

EXAMPLE 5

A barrier formulation was made fresh as in Example 4. The formulation was applied as a 2 cm wide strip to the upper part of plastic plant pots with a plastic brush. A total of 18 pots were treated, 9 with a thick (5 mm) salt strip and 9 with a thin (2 mm) one, and the pots were left to dry for 24 hrs. After drying, all pots were put into a shower for one hour. After removal from the shower, the thin-strip pots had lost most of their soap and some sides of the pots were bare. The thick soap strips were not visibly affected by the water treatment.

To evaluate the effectiveness of the barriers, 36 liter plastic tubs were set up containing vermiculite covered by paper toweling. The treated pots were filled with stones and vermiculite as were untreated, control pots. Three of the treated pots and three of the untreated pots were put in each tub. The pots were distributed evenly throughout the tub, but were spaced away from the wall to prevent access from the side. A slice of cucumber and fish flakes were placed on the top of each pot and the tubs were covered with a lid. Six slugs were placed in each tub, and three tubs were set up with the thick salt strips while three were set up with the thin salt strips.

The effectiveness of the salt strips in preventing slug feeding was assessed after 24 hrs. and after 6 days. After the 24 hr. assessment, the paper toweling was wetted and the cucumbers replaced. At the termination of the tub assessment, the wide layered pots were put outside for natural weathering. The data are shown in Table 5, illustrating the number of pots eaten from out of a possible number of 3.

TABLE 5

Example 5 Results

| | 24 Hours | | 6 Days | |
|---|---|---|---|---|
| TREATMENT | Treated | Controls | Treated | Controls |
| Thin strip No. 1 | 0/3 | 2/3 | 2/3 | 3/3 |
| Thin strip No. 2 | 0/3 | 0/3 | 3/3 | 3/3 |
| Thin strip No. 3 | 0/3 | 2/3 | 1/3 | 3/3 |
| Thick strip No. 1 | 0/3 | 2/3 | 0/3 | 3/3 |
| Thick strip No. 2 | 0/3 | 1/3 | 0/3 | 3/3 |
| Thick strip No. 3 | 0/3 | 1/3 | 0/3 | 3/3 |

EXAMPLE 6

Two corrals of one-foot diameter were constructed from Suncast® plastic lawn edging. The corrals were placed on a bare field having an abundance of slugs—primarily *Arion* and *Deroceras spp*. Each corral was partially filled with dirt and was furnished with a lettuce plant, a slug house, bran flakes, and cucumber slices. A barrier formulation (sodium laurate:sodium caprate, 7:3 ratio, 40% ai as applied) was applied, as a single, thick, 2.5 cm-wide and, to the exterior face of one corral; the second corral was not treated. During the course of the experiment, the weather was highly variable: a number of days were hot and dry, and a number of days were wet, providing 30 mm of precipitation. The data obtained, after a period of 3 weeks, are illustrated in Table 6.

TABLE 6

Cumulative Number of Slugs that Entered the Corrals

| Treatments | Slugs | Observations |
|---|---|---|
| Sodium laurate-caprate (7:3) | 0 | Some cracking and lifting by 7 days |
| Control | 31 | |

EXAMPLE 7

Three plastic garden trays, each measuring 26 cm by 52 cm by 6.5 cm (depth), were treated with a barrier formulation comprising a 7:3 ratio of sodium laurate and sodium caprate initially having 40% active ingredient. On each tray, the soap/barrier formulation was applied as a single, thick, 2.5 cm-wide band, just beneath the tray's lip. After the soap had dried for 1 hour, the three treated trays along with three untreated/control trays, were placed in a field infested by *Arion ater, Deroceras spp.*, and other slug species. The distance from the ground to the tray's lip was 5 cm. Each tray was furnished with wet soil, 4 lettuce plants, and dog food. During the course of the experiment, the weather was variable, although heavy rains dominated the weather pattern. The data obtained after a nine day period are illustrated in Table 7.

TABLE 7

| Cumulative Number of Slugs that Entered the Trays | | | |
|---|---|---|---|
| Treatment | REP 1 | REP 2 | REP 3 |
| Sodium laurate-caprate (7:3) | 0 | 0 | 0 |
| Control | 8 | 3 | 72 |

EXAMPLE 8

The trial was conducted inside a 36 L Rubbermaid® container. The bottom of the container was covered with wet vermiculite and paper towels. Previously, 4 pieces of veneer were virtually totally covered with a barrier formulation comprising 40% sodium laurate and sodium caprate at a 7:3 ratio. Three of the veneer pieces had been weathered outdoors for 2, 3, and 4 weeks, respectively. The fourth veneer piece had not been weathered. A horizontal barrier was formed across the container at its midpoint using the 4 pieces of veneer. Ten *Arion ater* were placed to one side of the barrier, while provisions—slug houses, water, and cucumber slices—were placed to both sides. The duration of the experiment was 10 days, and no slugs crossed the barrier, during this 10 day period.

It is understood that various modifications may be made to the invention disclosed and claimed herein without departing from its intended scope.

What is claimed is:

1. A chemical barrier composition for preventing terrestrial molluscs from crossing the barrier composition, consisting essentially of:

a solid substrate material having no ability by itself to chemically repel terrestrial molluscs; and a coating applied to cover the surface of the substrate material, the coating consisting essentially of (a) an active ingredient, present at least about 10% by weight of the coating composition, effective to irritate and prevent terrestrial molluscs from crossing the barrier, the active ingredient being formed of the sodium, potassium, or ethanolamine salts of monocarboxylic fatty acids having from 8 to 14 carbon atoms, coconut fatty acid, palm kernel fatty acid, or mixtures thereof, and (b) a solvent selected from the group consisting of water, alcohols, diols, triols, and mixtures thereof, the barrier composition having good weather resistance properties such that it does not rapidly dissolve and become ineffective upon exposure to moisture or rainfall.

2. The chemical barrier of claim 1 wherein the substrate material is formed of a plurality of separate and discrete articles, each having the coating applied thereto.

3. The chemical barrier of claim 2 wherein the active ingredient is a mixture of sodium laurate and sodium caprate at a ratio of about 7:3.

4. The chemical barrier of claim 2 wherein the substrate material is in the form of separate and discrete articles and the diameter of the articles is in the range of 3 mm to 5 cm.

5. The chemical barrier of claim 4 wherein the substrate material is selected from the group consisting of paper, plastic, paperboard, wood chips, pebbles, and dried foods.

6. A chemical barrier composition for preventing terrestrial molluscs from crossing the barrier composition, consisting essentially of:

an active ingredient, effective to irritate terrestrial molluscs and to prevent terrestrial molluscs from crossing the barrier composition, consisting essentially of the sodium, potassium, or ethanolamine salts of monocarboxylic fatty acids having from 8 to 14 carbon atoms, palm kernel fatty acid, or mixtures thereof, the active ingredient being present at least about 10% by weight of the barrier composition; and a solvent selected from the group consisting of water, alcohols, diols, triols, and mixtures thereof, the barrier composition having good weather resistance properties such that it does not rapidly dissolve and become ineffective upon exposure to moisture or rainfall.

7. The barrier of claim 1 wherein the composition is in the form of solid granules or flakes.

8. The barrier of claim 1 wherein the composition is in the form of a viscous, fluid material that rapidly hardens to a solid mass upon exposure to the environment.

9. The barrier of claim 6 wherein the active ingredient is a mixture of sodium laurate and sodium caprate at a ratio of about 7:3.

10. The barrier of claim 8 wherein the active ingredient is present at a concentrate in range of about 20 to 50% by weight of the total composition.

11. The barrier of claim 6 wherein the active ingredient is dispersed with a polymeric matrix.

12. A chemical barrier composition for repelling terrestrial molluscs, consisting essentially of:

an active ingredient, effective to irritate terrestrial molluscs and to prevent the terrestrial molluscs from traversing the barrier, the active ingredient being selected from the group consisting of sodium myristate, sodium laurate, sodium caprate, the sodium salt of palm kernel fatty acid, and mixtures thereof; the active ingredient present at a concentration of at least 50% by weight of the composition.

13. The composition of claim 12 further including a colorant.

14. The composition of claim 13 wherein the active ingredient is a mixture of sodium laurate and sodium caparate at a ratio in the range of 8:2 to 6:4.

15. The composition of claim 13 wherein the active ingredient is a mixture of sodium myristate and sodium caprate at a ration in the range of 8:2 to 6:4.

16. The composition of claim 13 wherein the active ingredient is a mixture of sodium myristate, sodium laurate and sodium caprate at a ratio in the range of 6:2:2 to 5:2:3.

17. The barrier of claim 12 wherein the active ingredient is dispersed within a polymeric matrix.

18. A method of preventing terrestrial molluscs from infesting and attacking plants, comprising the steps of providing a chemical barrier composition effective to irritate terrestrial molluscs and to prevent terrestrial molluscs from traversing the barrier, the composition being in the form of a solid or a viscous gel that hardens, comprising about 10 to 100% by weight of the composition of an active ingredient selected from the group consisting of the sodium, potassium, or ethanolamine salts of monocarboxylic acids having from 8 to 14 carbon atoms, coconut fatty acid, palm kernel fatty acid, and mixtures thereof, the barrier composition having good weather resistance properties such that it does not rapidly dissolve and become ineffective upon exposure to moisture or rainfall; and applying the barrier composition in a continuous strip about the perimeter of an area within which it is desired to prevent intrusion and infestation by terrestrial molluscs.

19. The method of claim 18 wherein the continuous strip is applied as a single strip having a width of at least 2 cm.

20. The method of claim 18 wherein the continuous strip is applied on the trunk of a tree.

21. A chemical barrier composition for preventing terrestrial molluscs from crossing the barrier composition, consisting essentially of:

a colorant;

a solid substrate material having no ability by itself to chemically repel terrestrial molluscs; and a coating applied to cover the surface of the substrate material, the coating consisting essentially of (a) an active ingredient, present at least about 10% by weight of the coating composition, effective to irritate and prevent terrestrial molluscs from crossing the barrier, the active ingredient being formed of the sodium, potassium, or ethanolamine salts of monocarboxylic fatty acids having from 8 to 14 carbon atoms, coconut fatty acid, palm kernel fatty acid, or mixtures thereof, and (b) a solvent selected from the group consisting of water, alcohols, diols, triols, and mixtures thereof, the barrier composition having good weather resistance properties such that it does not rapidly dissolve and become ineffective upon exposure to moisture or rainfall.

22. A chemical barrier composition for preventing terrestrial molluscs from crossing the barrier composition, consisting essentially of:

a colorant;

an active ingredient, effective to irritate terrestrial molluscs and to prevent terrestrial molluscs from crossing the barrier composition, consisting essentially of the sodium, potassium, or ethanolamine salts of monocarboxylic fatty acids having from 8 to 14 carbon atoms, palm kernel fatty acid, or mixtures thereof, the active ingredient being present at least about 10% by weight of the barrier composition; and a solvent selected from the group consisting of water, alcohols, diols, triols, and mixtures thereof, the barrier composition having good weather resistance properties such that it does not rapidly dissolve and become ineffective upon exposure to moisture or rainfall.

* * * * *